United States Patent [19]
McBrearty et al.

[11] Patent Number: 5,208,544
[45] Date of Patent: May 4, 1993

[54] NONINVASIVE DIELECTRIC SENSOR AND TECHNIQUE FOR MEASURING POLYMER PROPERTIES

[75] Inventors: Michael McBrearty, Hockessin; Stephen A. Perusich, Newark, both of Del.

[73] Assignee: E. I. Du Pont de Nemours and Company, Wilmington, Del.

[21] Appl. No.: 588,411

[22] Filed: Sep. 26, 1990

[51] Int. Cl.[5] ............................................. G01R 27/26
[52] U.S. Cl. .................................... 324/687; 324/688; 324/690; 324/663
[58] Field of Search ............... 324/663, 686, 687, 688, 324/690; 526/59, 60

[56] References Cited

U.S. PATENT DOCUMENTS

| | | | |
|---|---|---|---|
| 3,078,709 | 2/1963 | Clark | 324/690 X |
| 3,635,082 | 1/1972 | Prellwitz et al. | 324/690 X |
| 4,074,184 | 2/1978 | Dechene et al. | 324/690 X |
| 4,448,943 | 5/1984 | Golba et al. | 526/59 |
| 4,723,908 | 2/1988 | Kranbuehl | 324/687 X |

FOREIGN PATENT DOCUMENTS 0076441  4/1987  Japan.

Primary Examiner—Jack B. Harvey

[57] ABSTRACT

A sensor which allows dielectric measurements to be made on a high temperature product such as a molten plastic flowing in a conduit. It comprises a ceramic cylinder with an interdigitated electrode capacitor patterned into the inside wall. Uses of the sensor include continuous determination of copolymer composition and polymer viscosity (molecular weight) in a completely non-obstructive manner.

25 Claims, 8 Drawing Sheets

NONINVASIVE DIELECTRIC SENSOR AND TECHNIQUE FOR MEASURING POLYMER PROPERTIES

BACKGROUND OF THE INVENTION

1. Field of the Invention

This invention relates to a sensor which allows dielectric measurements to be made in a completely nonobstructive manner on a fluid such as molten plastic flowing in a conduit. In particular, it relates to a ceramic cylinder with an interdigitated electrode capacitor patterned into the inside wall. The sensor may be used for continuous determination of copolymer composition and polymer viscosity (molecular weight) of material flowing in a conduit.

2. Background

The dielectric properties of any polymer are frequency and temperature dependent functions of the dipolar and ionic atomic and molecular polarization. As a material is subjected to an alternating electric field, polar groups and free ions move and orient along the field lines, causing a buildup of charge at electrode surfaces. From measurements of the electrical current associated with this excess charge, the capacitance and dissipation of the system are computed. Using the exact geometry of the sensing volume, the dielectric constant and dielectric loss factor may be calculated. Dielectric properties can be used to measure polymer properties of interest such as thermal transitions, epoxy curing rates, water and additive concentrations, and voids in the polymer.

Such measurements can be made in a batch manner in the laboratory using flat capacitors, but to be useful as in-line sensors for application in the melt processing of thermoplastics, the capacitor should be made in a shape that can be installed in a conduit carrying molten polymer, and should be capable of reliable operation at the temperatures and pressures encountered with high-softening thermoplastics. The present invention provides such a sensor, preferably cylindrical, and shows it can be used in processing various molten polymers.

Dielectric spectroscopy is well known in the field of analytical chemistry. Interdigitated fringing field capacitors are also known, but the known devices are not suitable for use in a process pipeline Fr. 2,342,838 makes capacitance measurements on molten polymer, but the sensor is of a different design from the present sensor, with coaxial electrodes employing a core mandrel and the outer wall of a tube.

U.S. Pat. No. 4,448,909 and U.S. Pat. No. 4,448,943 apply capacitance cell measurements at the outlet of an extruder to control process variables in a thermoplastic compounding process. In contrast with the present tubular design, the sensor is a single parallel plate dielectric cell attached to the output end of an extruder. This arrangement generates substantial back pressure in the extruder, has poor product flow in the dead zone between the plates, and incurs measurement error due to deflection of the plates.

U.S. Pat. No. 3,846,073 uses a side-stream capacitance sensor with coaxial electrodes employing a core mandrel and the outer wall of a tube. The sensor is used to measure the vinyl acetate content of an ethylene/vinyl acetate copolymer.

An interdigitated comb electrode is commonly used for obtaining dielectric measurements on surfaces of materials and fluids. Probes of this type have been used for many years as moisture detection devices. U.S. Pat. No. 3,696,369 discloses an interdigitated electrode for moisture sensing. In the past few years these interdigitated probe structures were adapted to measure dielectric properties of materials. See, for example, *Society for the Advancement of Material and Process Engineering Journal,* 19, No. 4, July/August, 1983.

U.S. Ser. No. 07/274,461, filed Nov. 21, 1988, discloses a planar dielectric sensor having interdigitated electrodes for off-line analytical work.

No reference is known to the inventors which teaches the use of an interdigitated electrode conduit structure for use as a flow-through measurement sensor for fluid streams.

The present work involves (1) the invention of a new cylindrical, interdigitated dielectric sensor for nonobstructive, real-time process measurements, (2) a technique for relating the real component of the complex permittivity (dielectric constant or capacitance) to copolymer composition, and (3) relating the imaginary component (dielectric loss factor or dissipation) to the melt viscosity or molecular weight of polymers, providing instantaneous measurements of the melt viscosity or molecular weight in polymer melt processing.

With the present technique, a process stream flows across the electrode surface, an alternating voltage is applied between the two "combs" of the "interdigitated electrode" pattern, and the resulting alternating current is measured. In this fashion the field penetrates the surface of the material to a depth 2–5 times the distance separating the fingers in the interdigitated electrode array.

An alternating electric field, applied to a polymer, orients permanent and induced dipoles and separates positive and negative ions in the polymer. The dipole or ion movement is a function of the applied conditions (temperature, pressure), thermal properties (melting point, phase transitions, heat of fusion), rheological properties (flow rate, viscosity), physical properties (density, molecular weight, degree of polymerization), optical properties (index of refraction), and chemical properties (composition, reaction rate constant, activation energy).

Following are some of the problems of the prior art which this invention solves.

a) The need to avoid the introduction of obstructions into the pipeline, which is accomplished by using an interdigitated fringing field capacitor on the inside wall of a conduit, preferably a cylinder.

b) The need to minimize the abrasion of the electrodes by the process fluids, which is accomplished by orienting the electrodes in the flow direction and by recessing the electrodes so they are substantially flush with the inside wall of the cylinder. In addition, the inside surface of the sensor may be coated with a 0.1 micrometer deposited layer of alumina which protects the electrodes and allows for easier cleaning.

c) The need to provide field penetration a substantial distance into the product stream, so the measurement extends beyond the layer of product that is close to the pipe wall and therefore moves very slowly. This is accomplished by using an unusually large spacing between electrodes. The tendency for large spacing to reduce capacitance is counteracted by using a large electrode area.

d) The need to remove the heat-sensitive amplifier equipment from the vicinity of the sensor so high temperature melts can be measured. This is accomplished by using a current-to-voltage converter and a lock-in amplifier.

SUMMARY OF THE INVENTION

The invention is a sensor which allows dielectric measurements to be made on a fluid material flowing in a conduit, particularly when the product is at high temperature and pressure. It comprises a ceramic cylinder with an interdigitated electrode capacitor patterned into the inside wall. The electrodes are typically 0.050 inches (1.3 mm) wide with 0.050 inch (1.3 mm) spacing. This large spacing offers deep penetration of the alternating electric field into the material under test, improving the time response of the measurement, because the measurement is not restricted to the slow-moving layer adjacent to the wall of the cylinder.

The electrodes are recessed into the ceramic so that the electrode surfaces are substantially flush with the ceramic surface, reducing the potential for electrode erosion by abrasion. The electrodes are preferably oriented lengthwise inside the cylinder so the product flow is parallel to rather than perpendicular to the length of the electrodes, further reducing any tendency for erosion. Further protection against erosion may be applied in the form of a thin protective coating on the electrodes.

The sensor provides a means for controlling various processes, because it continuously monitors the capacitance and dissipation of the process stream.

In particular, the invention is a shielded sensor for making complex permittivity measurements in-line in a fluid conduit without obstructing the flow of the process fluid, said sensor having interdigitated fringing field electrodes recessed into a ceramic support conduit so the conductive electrode surfaces are substantially flush with the inner wall of the conduit, the active area of the sensing surface being 5 to 250 square centimeters ($cm^2$), and each pair of electrodes being spaced apart by 0.1 to 10 millimeters (mm), all materials used in the sensor being suitable for continuous service at temperatures of 200° C., 300° C., or even higher.

FIGURES

DETAILS OF THE INVENTION

Figure 1:
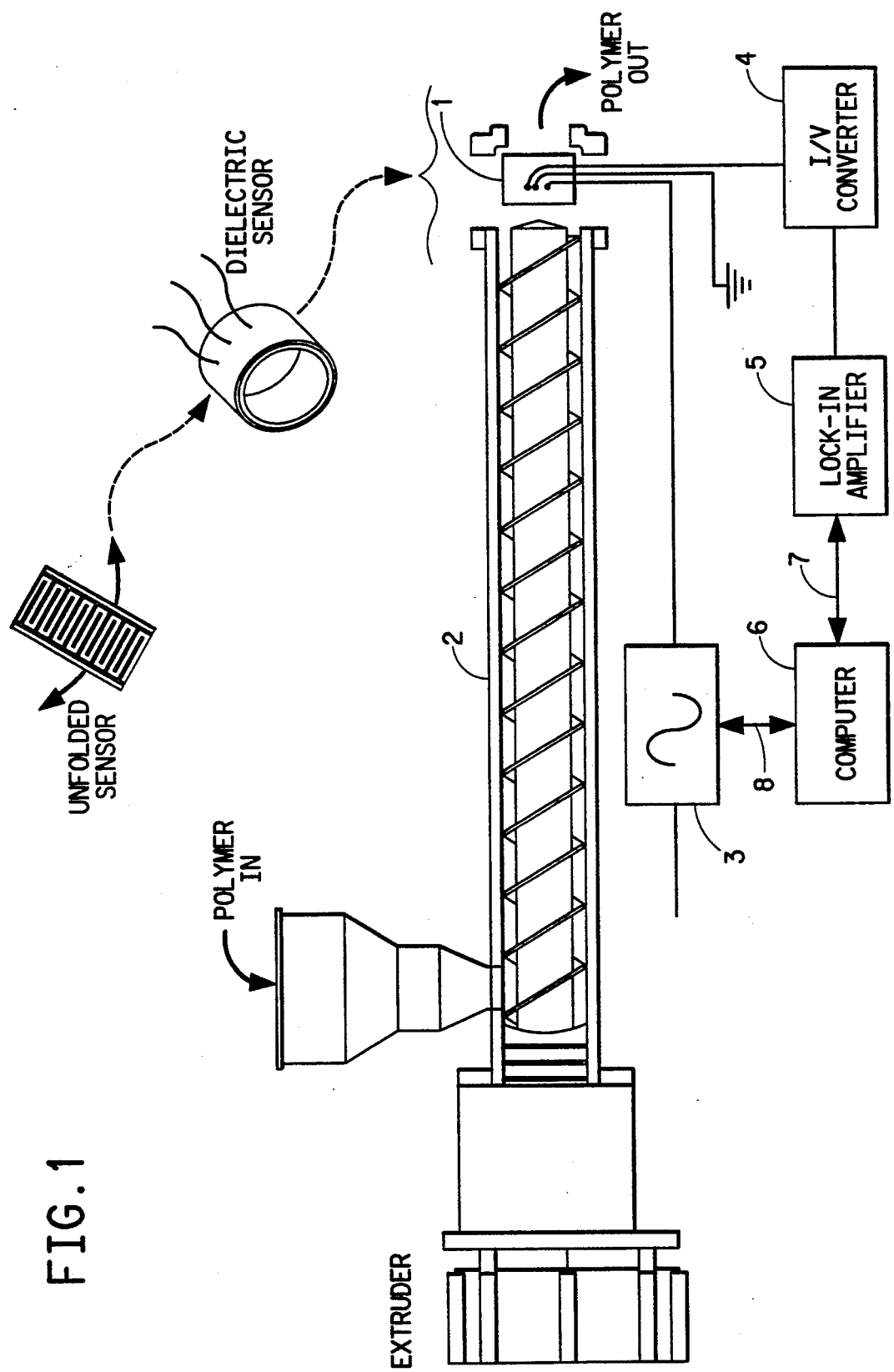
FIG. 1 depicts the sensor in the discharge of an extruder and a schematic of the circuitry employed to obtain useful information from the sensor.

The sensor of the present invention is generally cylindrical in shape but can be made in other configurations if desired.

It can be made and used in various sizes. Smaller inside diameter, shorter sensors would have smaller electrode area and, to maintain a measurable capacitance, would require smaller gap between electrodes. Larger diameter, longer sensors would have a larger electrode area and could allow a larger gap between electrodes to increase the thickness of the product layer subject to measurement. With a larger diameter for a given measurement depth, a smaller portion of the total flowing fluid will be analyzed, and the measured sample may not be fully representative of the entire sample. While there is no firm upper limit on inside diameter, it will usually be less than 8 centimeters (cm) in diameter.

When the inside diameter is smaller, the problem of patterning the electrodes on the inside of the conduit becomes more difficult, especially when the conduit is some shape other than circular in cross-section. While there is no firm lower limit on inside diameter, the sensor will seldom be less than 2 cm in diameter.

The length of the sensor will usually be between 2 and 15 cm, the gap between electrodes will usually be between 0.1 and 10 mm, preferably between 0.5 and 5 mm, and the active area of the sensing surface will usually be between 5 and 250 $cm^2$, preferably between 10 and 200 $cm^2$, most preferably between 40 and 80 $cm^2$.

The thickness of the sensor is sufficient to permit safe operation at temperatures and pressures of the application in which the sensor is employed. The needed wall thickness of the sensor (outside diameter minus inside diameter) for anticipated operating conditions can be calculated by those skilled in the art of piping design. It will vary with materials of construction.

The sensor operates in the fringing field mode; that is, the fringes of the electromagnetic field between the electrodes penetrate into the sample. The spacing of the interdigitated electrodes is selected to obtain maximum penetration of the fringing electromagnetic field into a significant fraction of the sample volume within the sensor while retaining a readily measurable capacitance between the electrodes. The average dielectric properties of this annulus shaped volume of sample are thus measured.

For a 4.5 cm diameter plastics extruder barrel, suitable dimensions of the sensor are: outside diameter of sensor 7.6 cm, inside diameter of sensor 4.5 cm, overall length of sensor 3.8 cm, 27 pairs of electrode fingers or "teeth", each having a width of 1.2 mm and a gap a 1.2 mm between electrodes. This spacing results in an effective measurement depth of about 0.6 cm into the polymer. For a 4.5 cm diameter cylinder and a 0.6 cm measurement depth, about 46% of the volume of polymer is measured. The measured capacitance for this alumina sensor was on the order of 70 picofarads (pF) in the absence of polymer and 80–90 pF in the presence of ethylene/vinyl acetate copolymer at 1 kHz at a processing temperature of 200° C.

Since most polymers are processed at melt temperatures in the range of 200°-400° C., it is desirable to have the sensor made of materials which can withstand these temperatures. For the structural support, a high-resistance, thermally stable organic polymer such as phenol/-formaldehyde, melamine/formaldehyde, aromatic polyimide, and the like may be successful in some instances. However, ceramic materials are preferred because of their excellent electrical properties, high modulus, and good resistance to high temperature. Suitable ceramics are alumina and Macor ® (Dow Corning), a machinable glass-ceramic. Another possibility is toughened zirconia.

The first step in making a sensor is to machine the structural shell, preferably ceramic, to the desired dimensions. In one embodiment, holes are then bored in the shell so that the electrical leads can be brought through the shell and connected to the electrode fingers. To help the sensor withstand higher pressures, it is better to omit drilling holes, which are stress risers. Instead, it is possible to pattern the electrodes so that electrical contact for one set is made at one end of the sensor and for the other set at the opposite end of the sensor.

Plating technology, known from such publications as *Electroplating Engineering Handbook*, (A. K. Graham, ed., van Nostrand Reinhold, N. Y. 1971) and *Electroless and other Nonelectrolyic Plating Techniques* (Chem. Tech. Review No. 171, J. I. Duffy, ed., Noyes Data Corp, 1980), may be adapted to place the electrodes on the inside of the sensor shell and to provide other conducting or non-conducting regions on the sensor.

For example, Du Pont Riston ® or Morton Thiokol photopolymer resist or equivalent photopolymer resist is applied to the inner and the circular regions around the wire feed-throughs of the outer surface of the shell. A pattern mask, with exactly the right dimensions in order to cover the inner surface with no gap or overlap, is then applied to the inner surface of the photochemical coating. Ultraviolet light is applied through the mask to cure the desired portions only. The mask is removed, then the pattern is developed by washing with a solvent suitable to remove the unexposed photochemical coating. The pattern is comb-shaped and disposed in an interdigitated pectinate configuration.

The entire outside surface is plated to provide electrostatic shielding. If wire feed holes are used, they are plated on the inner surfaces but are isolated from the outer electrostatic shield by the presence of a metal-free area around those holes. The method for patterning the electrodes can be used on the outside surface as well.

The next step is to plate the area not coated with polymer (uncoated area) with a metal which is to become the electrode.

Preferably the first step is to etch the uncoated area of the ceramic with hydrofluoric acid to create a sufficient groove so that, after plating and honing, the electrodes will be flush with the inside surface of the shell. Etching also is used to improve adhesion of the electrode to the ceramic. Approximately 6 micrometers of a conductive metal such as nickel (Ni) is applied to the inside and a ground conductor or electrostatic shield is applied to the outside of the support ceramic by electroless plating. Additional plating can be carried out if inspection shows that the metal does not completely fill the grooves. Groove depth should preferably be about 15 micrometers.

Preferably, sufficient gold to guarantee that the groove in the ceramic is more than completely filled is applied over the conductive metal on both the inner and outer surfaces by electroplating or electroless plating to prevent tarnishing of the Ni in the next step.

After plating, the remaining photoresist polymer is removed with stripper capable of dissolving photo-exposed resist without damaging the electrodes. The electrode surface is honed to a smooth finish, since an uneven surface would increase the risk that the sensor might be damaged by abrasion after it is placed in the moving process stream.

The electrodes are preferably oriented lengthwise inside the cylinder so the product flow is parallel to rather than perpendicular to the length of the electrodes, further reducing any tendency for erosion. On the other hand, by orienting the electrodes perpendicular to flow, the electric field would then be parallel to the flow so that ions and the bulk flow would move in the same direction. This may increase the measured signal.

Wires connecting the electrodes on the inner surface of the sensor to external electronic equipment are brazed into the gold-plated through-holes in the wall. High temperature solder may be used, but it limits the temperature of the sensor to a maximum of about 265° C., at which temperature the solder would melt. Brazing is the preferred method. Brazing material has a remelt temperature of 807° C. The gold prevents the tarnishing of the Ni during brazing.

In a preferred embodiment, the use of through-holes in the sensor wall. To accomplish this, the circuit pattern is made so that the metallization associated with one electrode (set of "fingers" or "teeth") extends around the edge of the sensor and is electrically connected to metallization covering one of the end faces (for instance, the upstream face) of the sensor. The metallization associated with the other electrode is similarly made to be contiguous with metallization on the other end face (say, the downstream face). In this way, the sensor can be connected to external measurement equipment by connecting wires to washer-shaped contacts pressed against the sensor body on the upstream and downstream faces. The sensor may be bolted in place between a pair of flanges on the process piping exiting the extruder using annealed copper shims or elastomer seals as washers. The shims may be gold plated to prevent chemical attack on the shims.

As in the previous design, the outside surface of the sensor is coated with a third metallization which is electrically isolated from the two discussed above, and which serves as an electrostatic shield to reduce electrical noise. The pressure rating of the sensor is elevated by omitting holes in the sensor.

The working surface (that over which the polymer flows) of the sensor may be further protected from abrasion without destroying the sensitivity of the sensor by application of a thin (0.2 to 10 micrometer) coat of $SiO_2$ or $Si_3N_4$ or sputtered alumina ($Al_3O_3$).

One skilled in the art will appreciate that various alternative methods for manufacturing the sensor are possible. The preferred embodiment already mentioned is to avoid the mechanical weakness introduced by drilling holes in the ceramic support for electrical leads, by making the electrical contacts at the opposite ends of the sensor. Then metallic contacts at each end of the sensor can be used as the leads to the measurement equipment. Eliminating wire feed holes improved the pressure rating of the sensor of Example 2 to 21 megapascals (MPa). This change also eliminated the difficult step of aligning the circuit pattern photomask with the wire feed holes.

FIG. 1 depicts a sensor (1) in the discharge of an extruder (2). A sine wave generator (3), such as a Hewlett-Packard HP 3326A, is used to drive the sensor. A current-to-voltage converter (4) and a lock-in amplifier (5) are used to measure the amplitude and phase angle of the resultant alternating current. These measurements allow the computation of the capacitance and dissipation values of the polymer as a function of frequency and temperature. Dielectric measurements are made over a range from 0.5 hertz (Hz) to 200 kilohertz (kHz) at 15 frequencies: 0.5, 0.7, 1.0, 5.0, 10, 100, 500 Hz, 1, 5, 10, 20, 50, 100, 150, and 200 kHz at 160°–285° C. This series of measured values thus establishes a frequency spectrum of both the real and imaginary parts of the complex permittivity.

The I to V converters used amplify the signal either $10^2$ or $10^6$ times, depending on the frequency, while converting a current signal to a voltage signal. The converters may be Ithaco Model 1641 preamplifiers Or the like. A Cytec Model LXB/128 switching unit, not shown in figure, may be use to facilitate switching to the proper converter based on frequency. Equivalent equipment may be substituted.

The signal from the I to V converter (4) is fed to an Ithaco 3961B two-phase lock-in amplifier (5), which filters out noise, selects the signal component at the reference frequency, and segregates in-phase and out-of-phase portions of the signal. A personal computer (6) attached to the sine wave generator and the lock-in amplifier through a general purpose interface bus (GPIB) can be used to calculate capacitance, dissipation, and dissipation factor based on the signal from the lock-in amplifier (7) and the frequency and voltage set for the sine wave generator (8). Dissipation factor, or tan $\delta$, is defined as the in-phase current divided by the out-of-phase current. Equivalent equipment may be substituted.

With a larger switching matrix, one set of electronic equipment would be adequate to operate several sensors on several extruders. The output from the computer can be used to control a process or extrusion variable that would adjust the properties of the polymer to the desired range, or it could be used to make a record of the extrusion run, in terms of product composition or melt viscosity, for example.

EXAMPLES

Figure 2:
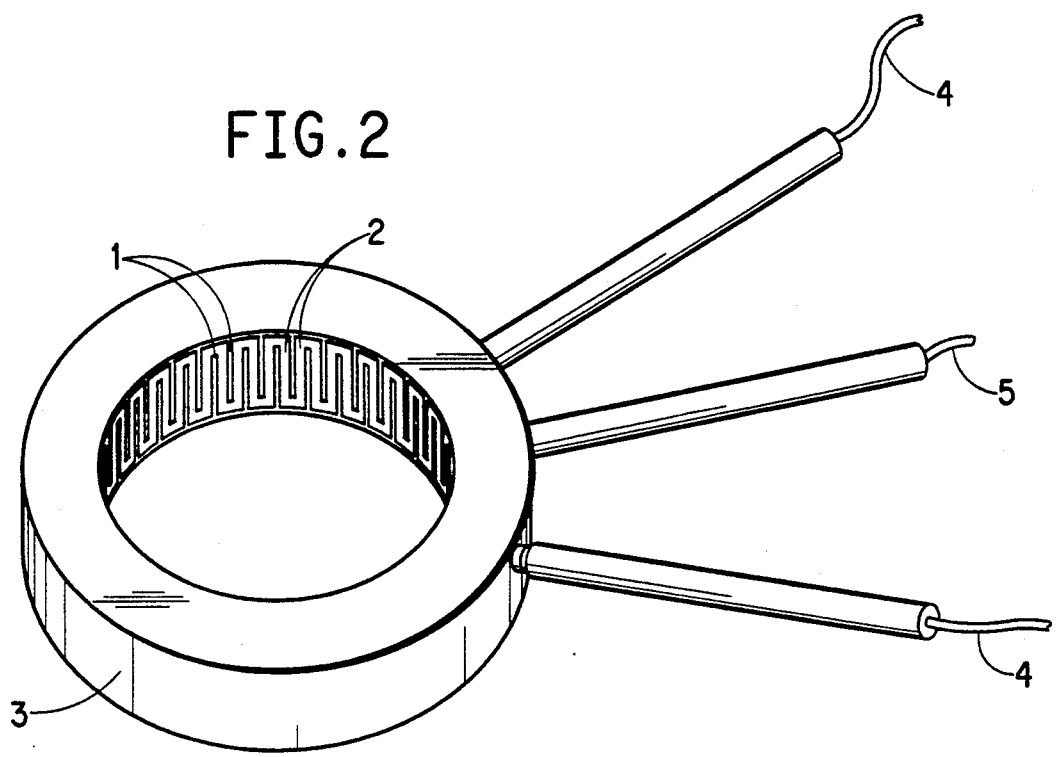
FIG. 2 depicts the Macor ® sensor with electrical leads passing through holes in the sensor shell wall.

Example 1: Preparation of a sensor made of Dow corning Macor ® glass bonded ceramic The sensor, pictured in FIG. 2, was made for either a 3.8 cm diameter single-screw Killion extruder or a twin-screw Haake extruder. It had an outside diameter of 5 cm, inside diameter of 3.8 cm, overall length of 3.4 cm, and 24 pairs of electrode "teeth" (1), each having a width of 1.2 mm and a 1.2 mm gap (2) between electrodes. This spacing provides an effective measurement depth of about 0.6 cm into a polymer flowing through the bore of the sensor. Thus about 55% of the volume of polymer can be measured. When installed on the Haake extruder, the measured capacitance for this sensor at 275° C. in the absence of polymer was 45±5 pF at 1 kHz and 30±2 pF at 100 kHz.

The first step in making the sensor was to machine the structural shell, made of Dow Corning Macor ®, to the desired dimensions. Two holes were then bored in the shell for electrical leads. Morton Thiokol photopolymer resist was applied to the inner surface and to the small regions surrounding the wire feeds to the electrodes of the outer surface of the shell.

A pattern mask, with the right dimensions in order to cover the inner surface with no gap or overlap, was then applied to the inner surface of the photochemical coating. Ultraviolet light was applied through the mask to cure the desired portions only. Then the pattern was developed by standard techniques to remove the unexposed photochemical coating. The pattern of the area left uncoated (uncoated area) was comb-shaped and disposed in an interdigitated pectinate configuration. The inner orifice of the two holes drilled through the shell were positioned so as to contact the uncoated area in a manner so that one was aligned to make electrical contact with one set of "teeth" and the other was aligned to make electrical contact with the opposing set of "teeth".

Next the uncoated area was plated with Ni, which was to become the electrode. This process was accomplished in several steps. First, the uncoated area of the ceramic was etched with aqueous hydrofluoric acid to create a groove approximately 15 micrometers deep for the electrodes. Then the Ni electrodes were electroless plated to the inside and a ground conductor or electrostatic shield (3) was applied to the outside of the support ceramic. The photoresist, etching and plating steps were performed by E. Perry, R & D Consultants, 33 West Boxelder, Suite 116, Chandler AZ 85224.

The entire outside surface was plated with approximately 6 micrometers of Ni to provide electrostatic shielding. The wire feed holes were plated on the inner surfaces but were isolated from the electrostatic shield by absence of metal around those holes.

Gold (about 10 to 25 micrometers thick) Was applied over the nickel on the inner and outer surfaces by electroless or electroplating to prevent tarnishing of the nickel in the next step.

After plating, the remaining photoresist polymer was removed with the stripper solution to dissolve exposed resist without damaging the electrode.

The electrode surface was honed to a smooth finish, flush with the ceramic.

Wires (4) connecting the electrodes on the inner surface of the sensor to external electronic equipment were brazed into the gold-plated through-holes in the wall. The gold prevented the tarnishing of the nickel during brazing. A ground wire (5) was brazed to the gold-plated Ni electrostatic shielding.

Example 2: Preparation of an alumina sensor

Figure 3:
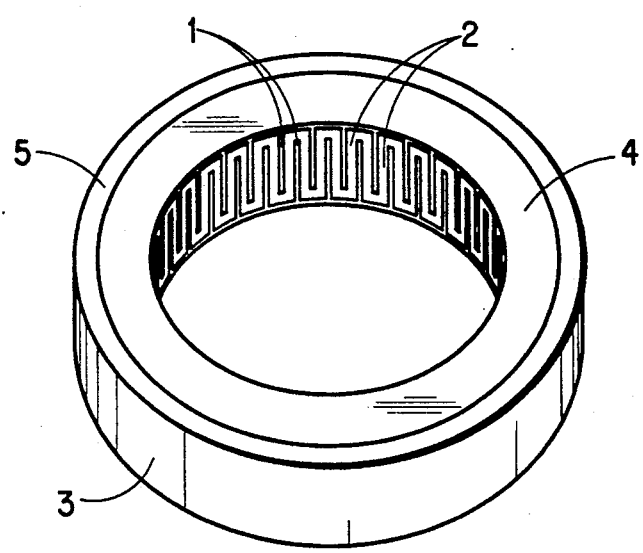
FIG. 3 depicts the alumina sensor with a means for conducting electrical current to and from the electrodes without holes in the sensor shell wall.

In this example, the use of holes through the ceramic support for electrical leads was avoided by taking the electrical leads to the opposite ends of the sensor (see FIG. 3). Then a metallic contact at each end of the sensor served as the lead to the measurement equipment. Eliminating wire feed holes, which serve as stress risers, improved the pressure rating of the sensor to 21 MPa. This approach also eliminated the difficult step of aligning the circuit pattern photomask with the wire feed holes.

In this case the ceramic sensor was made of alumina, and the dimensions of the sensor were 4.5 cm inside diameter, 7.6 cm outside diameter, 3.8 cm long, 27 pairs of electrode "teeth" (1), each having a width of 1.2 mm and a 1.2 mm gap (2) between electrodes.

Electroplating of interdigitated pectinate configuration and the outer electrostatic shield (3) was performed as in Example 1. In this case, however, the holes were not drilled, plating was extended to the faces (4) of the shell, and a 2.5 mm space or ring (5) was machined at the outer circumference of each face to prevent electrical contact with the outer electrostatic shield. This insulating ring could have been achieved using the photomasking technique employed to plate the electrodes.

When the sensor is bolted in place between flanges of a material suitable to be used in the process stream (a housing of stainless steel or Hastelloy, for example), metallic rings (copper in the examples of this case) that contact the plated faces, but not the outer electrostatic shield, form the electrical contact provided by the wires extending through the holes in Example 1. Wires from these copper rings form the leads to the measurement equipment. Gaskets made of nonconductive materials that are chemically and thermally compatible with the system (two Du Pont Kalrez ® gaskets with an alumina spacer between them on each side of the sensor in the examples of this case) are used to insulate the sensor and contact rings from the housing. These gaskets should be of sufficient thickness to avoid capacitive coupling to the housing. The electrostatic shield is grounded.

Example 3 This example shows that the sensor of the present invention can be used to detect the comonomer content of a polymer The sensor of Example 1 was mounted between flanges at the exit of the static mixer section of a 22 mm single screw Killion extruder, so as to permit the melted polymer to flow through the bore of the sensor.

FIG. 1 depicts the setup used in this example. A Hewlett Packard HP3326A sine wave generator was used to drive the sensor. A current-to-voltage converter with a lock-in amplifier was used to measure the amplitude and phase angle of the resultant alternating current exiting the sensor. From these measurements, the capacitance and dissipation values of the polymer were calculated continuously using a personal computer as a function of frequency and temperature. Dielectric measurements were made over a range from 0.5 Hz to 200 kHz at 15 frequencies: 0.5, 0.7, 1.0, 5.0, 10, 100, 500 Hz, 1, 5, 10, 20, 50, 100, 150, and 200 kHz at 160°–285° C. This series of measured values thus established a frequency spectrum of both the real and imaginary parts of the complex permittivity.

The I to V converters generated a voltage signal either $10^2$ times (converter being a 100 ohm resistor) or $10^6$ times (Ithaco Model 1641 converter) the current flowing through the sensor, depending on frequency. A Cytec Model LXB/128 switching unit, not shown, was used to facilitate switching from one convertor to the other based on the frequency of the signal from the sine wave generator.

The signal from the I to V converter was fed to an Ithaco 3961B two-phase lock-in amplifier, which filtered out noise, selected the signal component at the reference frequency, and segregated in-phase and out-of-phase portions of the signal.

Figure 4:
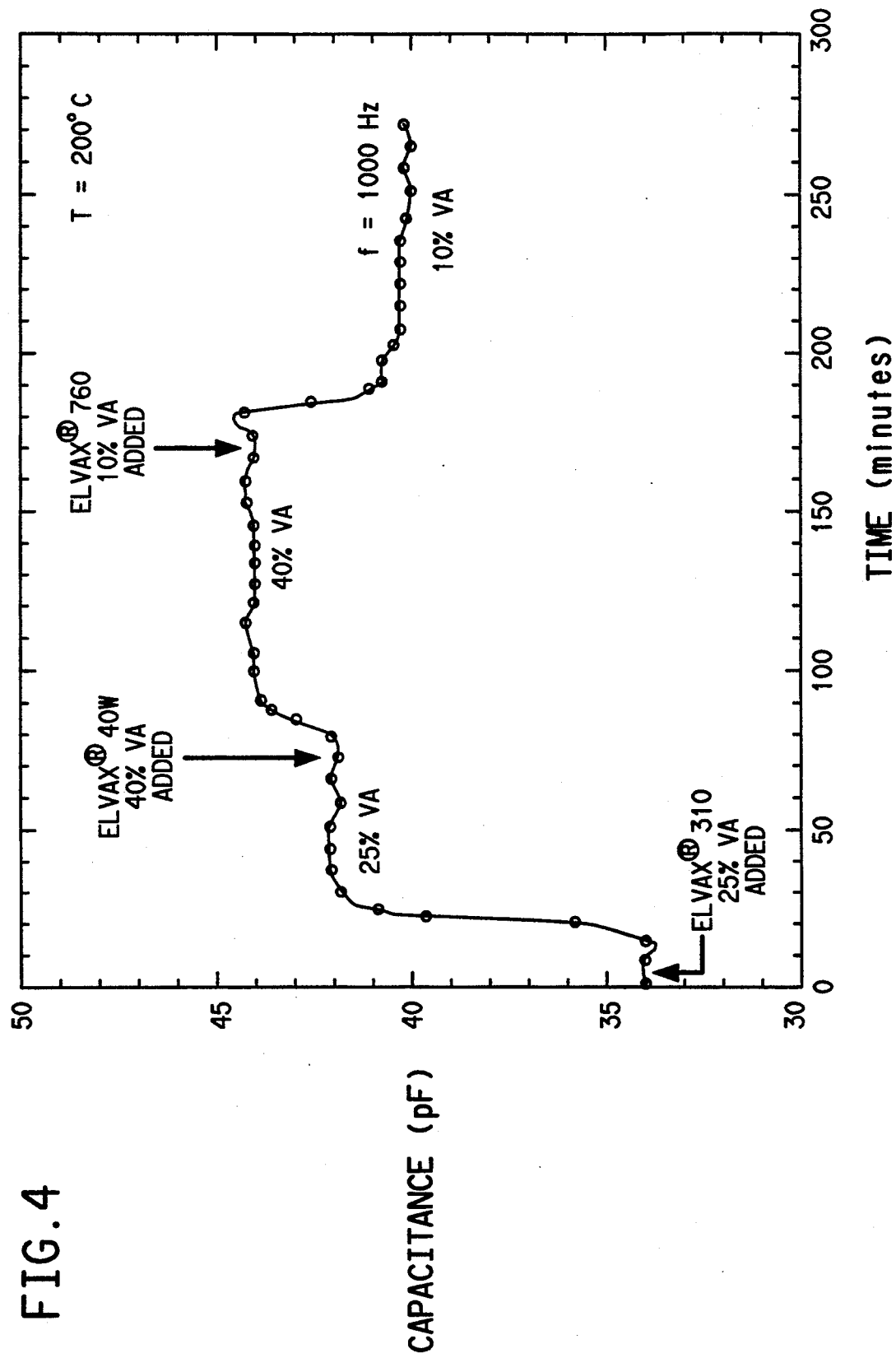
FIG. 4 is a plot of capacitance versus time for a flowing stream of Du Pont Elvax ® ethylene-vinyl acetate copolymer in which the content of vinyl acetate was increased in steps.

FIG. 4 is a plot of the capacitance measured over time at 200° C. and 1000 Hz for various grades of Elvax ® ethylene/vinyl acetate copolymer. Initially, while the Killion extruder was empty (time =0), the background capacitance ($C_o$) measured 34 pF, a value including the air, ceramic, and other stray capacitances. The relative dielectric constants were calculated using the equation, $\epsilon' = C/C_o$, where C and $C_o$ are capacitance.

A polymer containing 25% vinyl acetate (VA) and having an intrinsic viscosity of 1.04 was added 6 minutes after the run started. At 30 rpm, the polymer took approximately 5 minutes to travel from the hopper through the screw and static mixer sections to the sensor. At this time the measured capacitance (dielectric signal) increased dramatically. After 10 minutes, a plateau value of 41.8 pF was achieved. At 74 minutes, a polymer with 40% VA and 1.44 viscosity was added and another plateau was obtained at 44.1 pF. Finally, at 171 minutes a polymer with 10% VA and 2.8 viscosity was added and a lower plateau was achieved at 40.2 pF.

The plateau values of capacitance are approximately equal to plateau values obtained in measurements taken on individually-run polymer samples. The frequency range examined was from 0.5 to 200,000 Hz. Below 1000 Hz the aforementioned trends were still present, but the plateau value was not as stable. At frequencies at or above 1000 Hz, the signals were very stable and consistent.

The above experiment was duplicated using the alumina sensor of Example 2, with comparable results.

Figure 5:
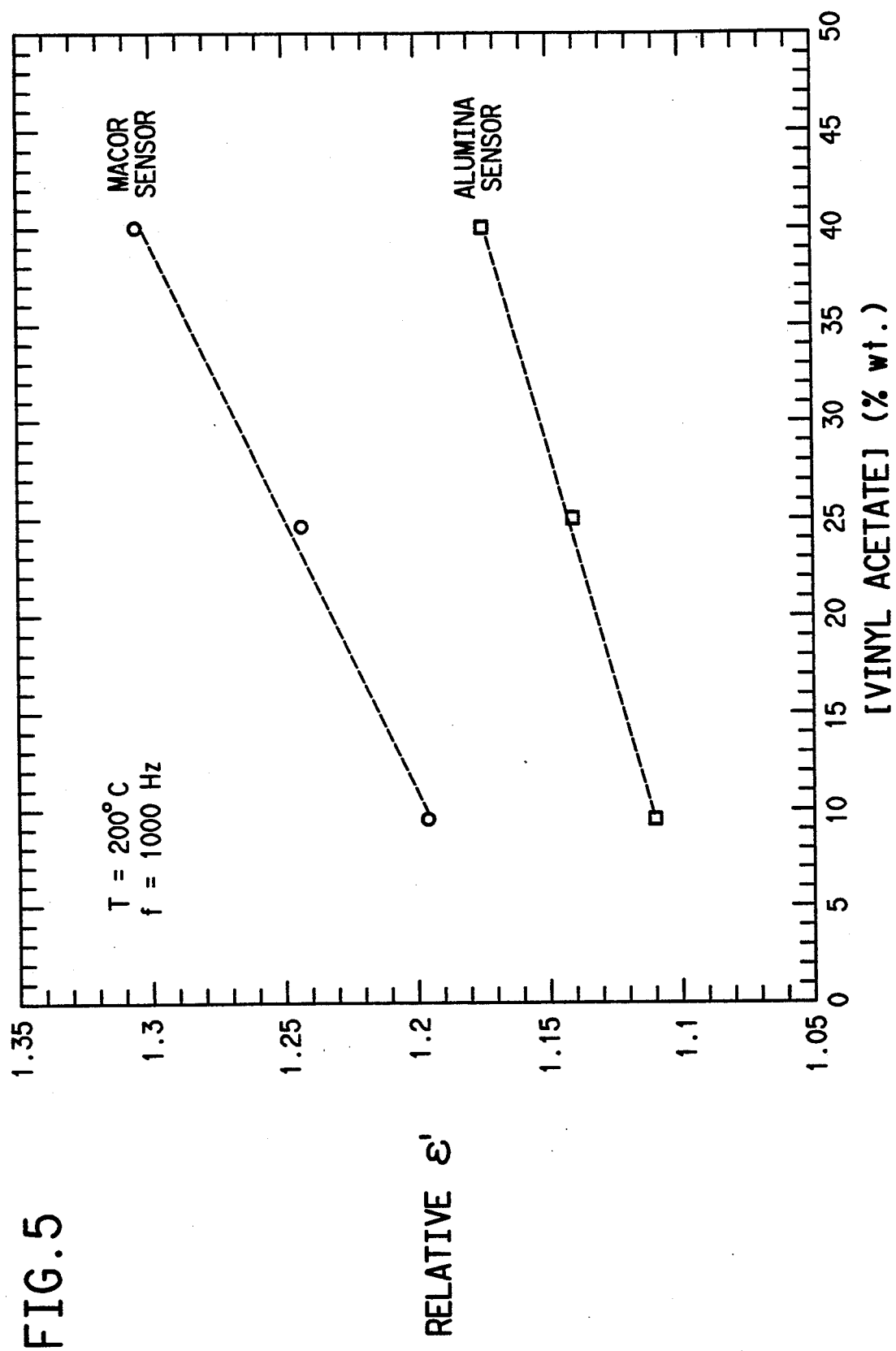
FIG. 5 is a plot of relative dielectric constant ($\epsilon'$) versus weight percent vinyl acetate in Du Pont Elvax ®.

The plateau values from the two experiments are plotted in FIG. 5 versus the relative dielectric constant ($\epsilon' = C/C_o$). Both experiments using the two sensors yielded a linear relationship between $\epsilon'$ and vinyl acetate concentration [VA].

Example 4: This example shows that the sensor can be used for the measurement of melt viscosity of a polar fluoropolymer In this example, in-line dielectric data were compared with off-line capillary viscometry data. The polymer used was a copolymer of tetrafluoroethylene and $CF_2 = CFOCF_2CF(CF_3)OCF_2CF_2SO_2F$ with an equivalent weight of 1149. The reference capillary rheology measurements were performed at 220°, 240°, 260°, and 275° C. over a range of shear rates from 1 to 50,000 /second.

The in-line dielectric data were obtained using the sensor of Example 2 at the same four temperatures, so the viscosity was adjusted by temperature without changing the composition of the polymer. The dissipation increased with temperature at low frequencies. At 275° C., bubbles were formed, disturbing the measurement.

It is known from the art that the following equation defines the relationship between apparent viscosity ($\eta$) and dielectric loss factor ($\epsilon''$):

$$\omega \epsilon_0 \epsilon'' = \left(\frac{q^2 N}{6\pi r}\right)\left(\frac{1}{\eta m}\right).$$

Assuming $\epsilon'' = K_1 D$, $$\text{then } D = \left(\frac{q^2 N}{6\pi r \omega \epsilon_0 K_1}\right)\left(\frac{1}{\eta m}\right) = \frac{K}{\eta m}.$$

Thus, $\log D = -m \log \eta + \log K$.

where:
$\omega$ = frequency (radians/second)
$\epsilon_0$ = permittivity in a vacuum (Farads/meter)

Figure 6:
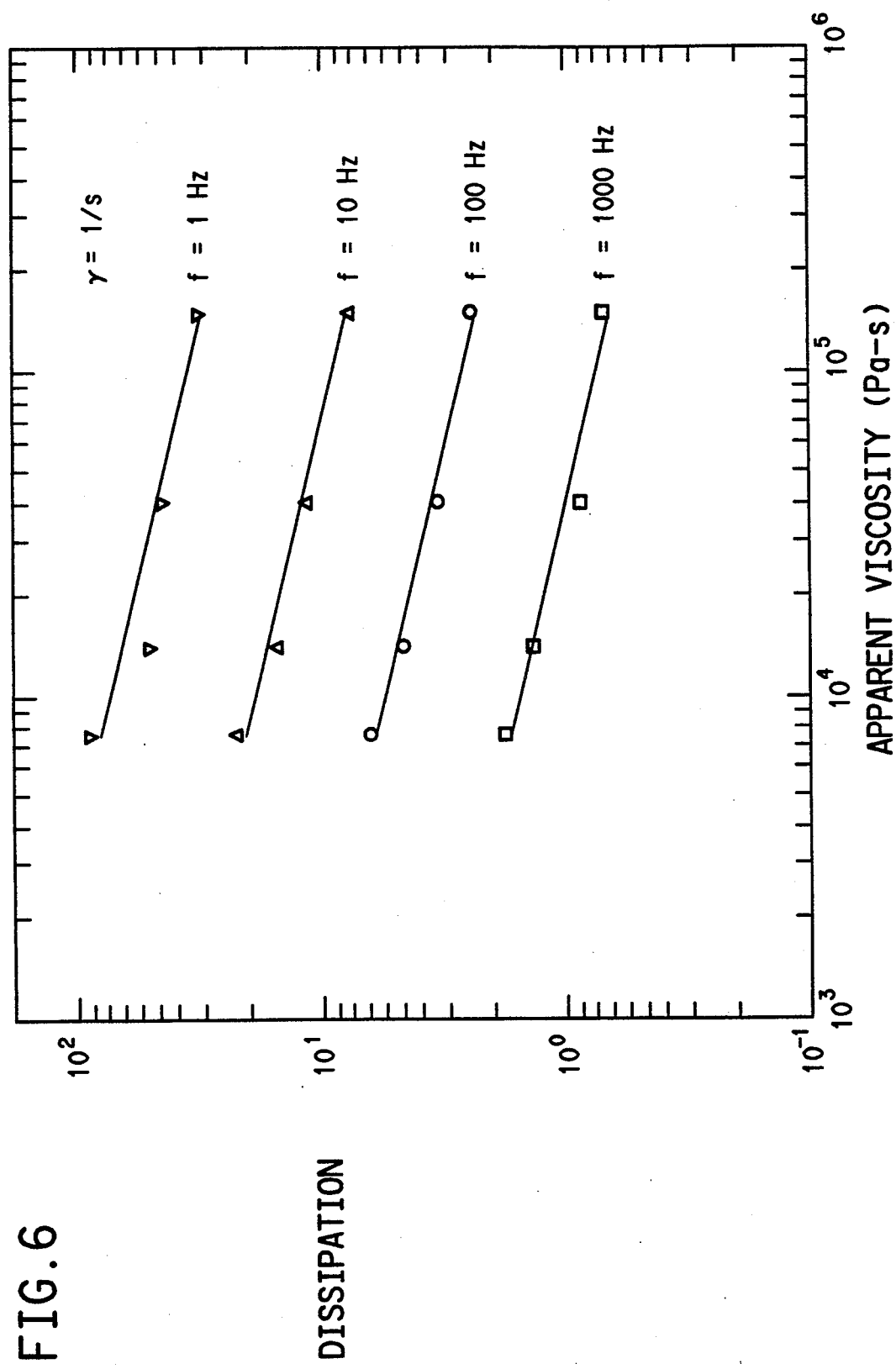
FIG. 6 is a plot of the log of dissipation (D) versus the log of apparent viscosity ($\eta$) of a copolymer of tetrafluoroethylene and $CF_2=CFOCF_2CF(CF_3)OCF_2CF_2SO_2F$.

$\epsilon''$ = dielectric loss factor
q = electrical charge (coulombs)
N = ion concentration (moles/cm3)
r = ion radius (cm)
$\eta$ = apparent viscosity (pascal seconds)
D = dissipation
m, K, $K_1$ = constants The experimental data of FIG. 6 fit the above theoretical predictions. The curves in FIG. 6 were plotted by matching capillary viscosity and dissipation data at the same temperatures at different shear rates. Alternatively, the in-line and off-line data could have been matched at the same shear rates and different shear stresses to obtain additional data. Note that along any given line the four data points represent four independent temperatures. Thus for a given sample, the dielectric dissipation as measured with the sensor of this invention is linearly proportional to the melt (apparent) viscosity on a log-log plot as shown by experiments and predicted by theory. A duplicate run gave nearly identical results.

Example 5: This example shows that in-line measurements of viscosity can be made using a non-polar polymer One way to vary the rheological properties of the polymer without changing its composition is to alter the molecular weight. In this way, a study of the dependence of dissipation (D) on viscosity ($\eta$) can be made without affecting the capacitive signal. Polyethylene was chosen for this study because of its relatively non-polar structure and its availability in various molecular weight ranges.

The polyethylenes used and their rheological properties were measured in-line with the sensor of Example 2 and off-line with a capillary melt viscometer at 220° C. At a 50 rpm extruder screw speed, the average flow velocity in the sensor region was calculated to be about 1.95 cm/min. In a broad sense, comparison of this flow velocity to the velocity through a capillary should give an approximation between dielectric and viscometer data. Likewise, comparisons could be made between shear rates or between shear stresses. From the capillary viscometry data (at 1.8 cm/min and 220° C.) and melt flow data, the critical off-line data are summarized below.

| Polymer | Apparent Viscosity (Pa · s) | Melt Index (g/min) |
| --- | --- | --- |
| Dowlex ® 2505 | 39 | 85 |
| Tenite ® 1390P | 87 | 15 |
| Rexene ® 2030 | 151 | — |
| Dowlex ® 2535 | 259 | 6 |
| Alathon ® 20 | 259 | 1.9 |

It is expected that as the viscosity increases, the dissipation should decrease. The capacitance for all these samples should be constant since the composition is the same, barring the effect of additives or impurities.

The five polyethylene samples of various viscosities were tested twice with the in-line sensor of Example 2, and the results were compared with capillary viscometry off-line analytical data. In both extruder runs, a better correlation was obtained at higher screw speeds and lower temperatures.

The first run was performed at 240° C., 100 Hz, and 20 and 100 rpm (revolutions/minute of the screw). The dissipation generally decreased with apparent viscosity. The best correlation was a linear dependence between log D and log $\eta$ at 100 rpm.

Figure 7:
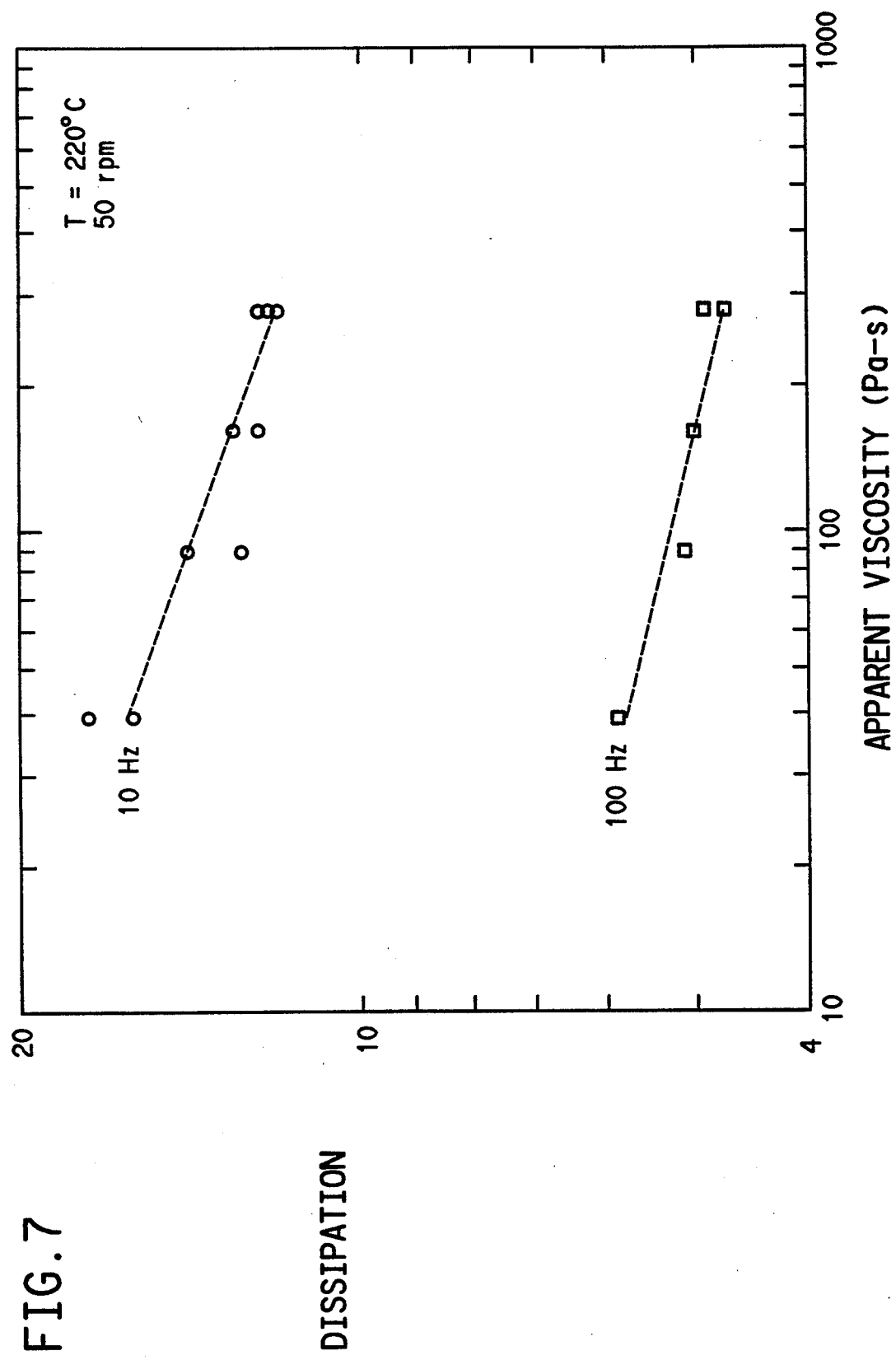
FIG. 7 is a plot of the log of dissipation (D) versus the log of apparent viscosity ($\eta$) for polyethylene of different molecular weights.

For the second run, the temperature was decreased to 220° C. and the screw rate was 50 rpm. The measuring frequency was alternated between 10 and 100 Hz. The plateau dissipation values are plotted in FIG. 7 versus off-line apparent viscosity as measured with a capillary melt viscometer. Again the dissipation generally decreased with apparent viscosity. The dashed lines are least square fits to the data.

Examples 6 and 7

The following examples show the utility of employing dielectric data for making various measurements in a non-flowing system. Based on the above examples, it is anticipated that the sensors of Example 1 and Example 2 can be used for these measurements in a flowing system.

Example 6

While the sensor was being developed, batch experiments were done with commercially available equipment using flat electrodes from Micromet Instrument, Inc. Cambridge, Mass. Three types of sensor were used: low conductivity (model 222S, $10^{-16}$ to $10^{-6}$ per ohm per cm), mid conductivity (model 230S, $10^{-14}$ to $10^{-4}$ per ohm per cm), and high conductivity (model 240S, to $10^{-1}$ per ohm per cm). A Compaq personal computer was used to control the frequency of the input voltage and the time over which measurements were to be taken. The current resulting from the sensor was sent back to a dielectrometer and the data were sent to the computer, analyzed, and plotted.

To obtain dielectric data, a polymer pellet or film was placed on a dielectric sensor and sandwiched between two 76 micrometer sheets of Teflon ® fluorocarbon resin. The assembly was then placed in a vacuum oven. A glass insulator and 440 gram (g) stainless steel weight were placed on top of the upper sheet of Teflon ® to control the rate of heat transfer to the polymer and to insure intimate contact between the polymer and electrodes.

To perform an experiment the polymer was first dried overnight under 50-65 cm of vacuum, using a nitrogen purge. The drying temperature depended on the polymer used. Then the temperature was quickly increased to above the melting point of the polymer, and the molten polymer was allowed to cool at a controlled rate. Dielectric data were obtained throughout the temperature cycle.

Figure 8:
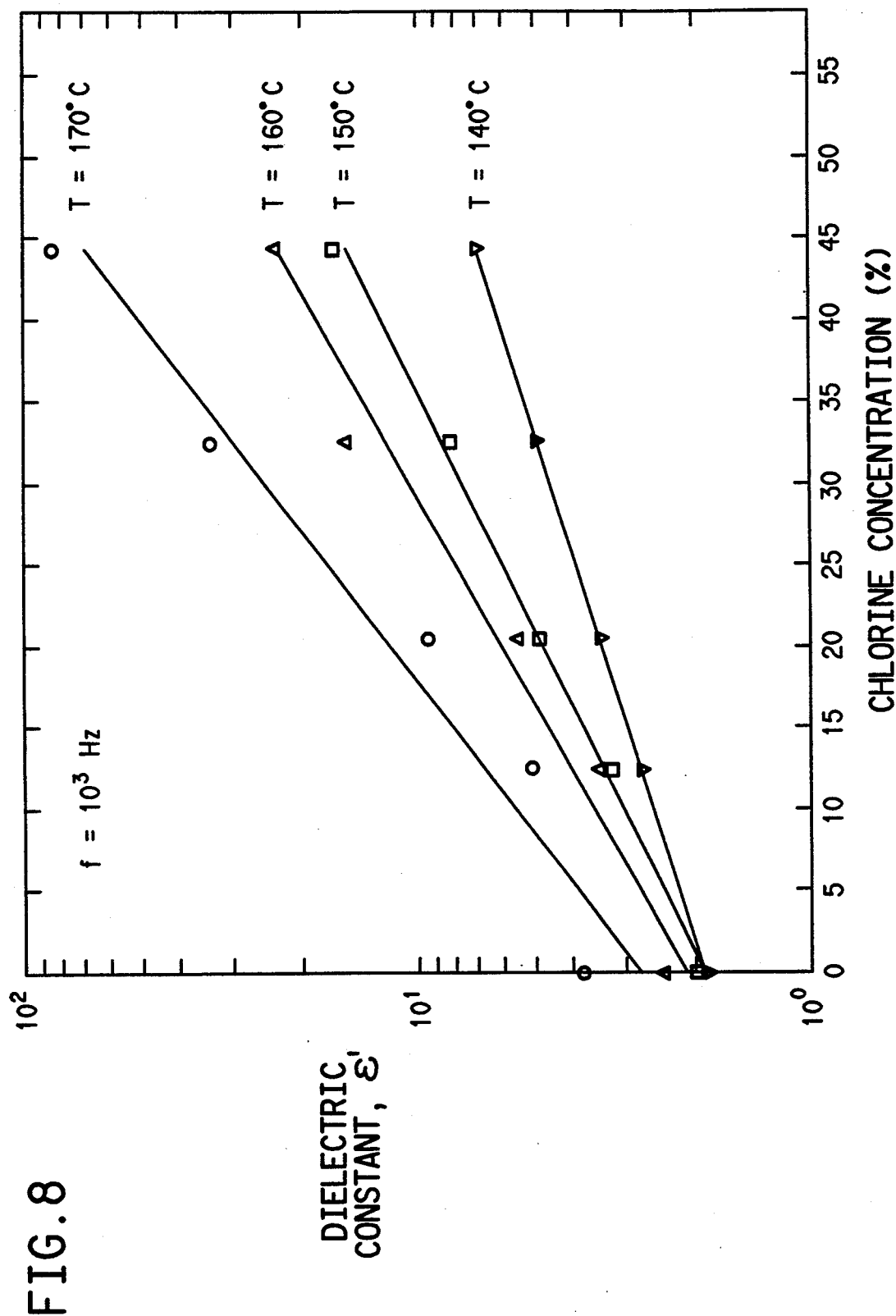
FIG. 8 is a plot of dielectric constant versus chlorine content for various chlorosulfonated polyethlene samples.
Figure 9:
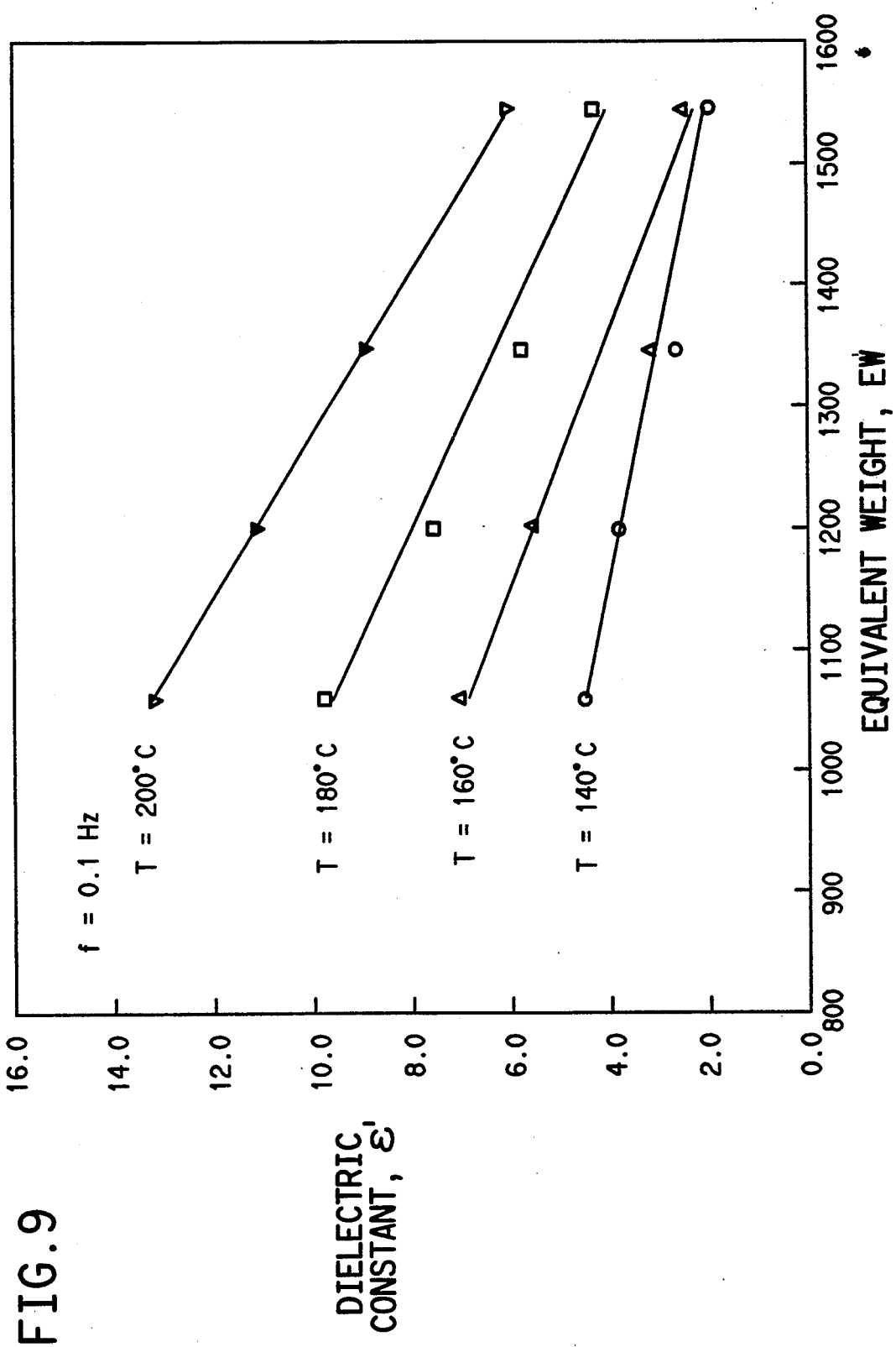
FIG. 9 is a plot of dielectric constant versus equivalent weight for copolymers of tetrafluoroethylene and $CF_2=CFOCF_2CF(CF_3)OCF_2CF_2SO_2F$.

Experiments were carried out with chlorosulfonated polyethylene powders with chlorine (Cl) concentrations between 12.5 and 43.9 weight percent (wt %), as determined by three methods: weight gain during synthesis, IR spectrophotometry, and the Schoeniger Combustion Method (a modified IR technique). Experimental data are shown in FIG. 8. Polyethylene was used for a sample free of Cl. At both 1000 Hz and 10,000 Hz a linear relationship was observed between the dielectric constant above the melting point and the known Cl content. This shows that dielectric measurements can be used to measure Cl content in this polymer. For this polymer, high frequency provides greater sensitivity.

Example 7

This work shows that the sensor of the present invention can be used to detect the comonomer content of a polymer. It differs from Example 3 in the functional group of the comonomer and in the fact that the polymer is perfluorinated.

The polymer used was the copolymer of tetrafluoroethylene and $CF_2=CFOCF_2CF(CF_3)OCF_2CF_2SO_2F$. Four copolymer samples of known equivalent weight 1064, 1196, 1346, and 1545 were individually heated to 220° C. and pressed onto a flat Micromet Model 222S low conductivity sensor. A Compaq personal computer was used to control the frequency of the input voltage and the time over which measurements were to be taken. The current resulting from the commercial sensor was sent back to a dielectrometer and the data were sent to the computer, analyzed, and plotted.

After lamination to the sensor, the polymer was heated past its softening point and then cooled at 1° C./min to obtain dielectric data at 0.1 to 10,000 Hz. Data for 200° C. and 0.1 Hz are shown in the attached FIG. 8. These data show that, at least at this temperature and frequency, equivalent weight (comonomer content) can be measured by measuring dielectric constant.

We claim:

1. A sensor for making complex permittivity measurements in-line in a fluid conduit without obstructing the flow of the process fluid, said sensor comprising a non-conductive shell having a bore therethrough, a pair of interdigitated fringing field electrodes on the inner surface of the shell, the electrodes being spaced from each other by 0.1 to 10 millimeters, an electrostatic shield on the outer surface, and means for conducting electrical current to one electrode and from the other electrode.

2. The sensor of claim 1 wherein the shell is cylindrical and the interdigitated fringing field electrodes are recessed into the inner surface of the shell sufficiently to be substantially flush with the inner wall of the shell.

3. The sensor of claim 2 wherein the inner surface of the shell has an area of 5 to 250 cm$^2$.

4. The sensor of claim 2 wherein all materials used in the sensor are suitable for continuous service at temperatures greater than about 200° C.

5. The sensor of claim 2 wherein the interdigitated electrodes have a long direction which is parallel to the axis of the cylinder.

6. The sensor of claim 4 wherein the material of the shell is a temperature-resistant ceramic.

7. The sensor of claim 2 wherein there is a thin coating on the electrodes to protect them against abrasion.

8. The sensor of claim 4 suitable for continuous service at 300° C. or higher.

9. The sensor of claim 2 wherein the means for conducting the electrical current comprises conductors that pass from the outside to the inside of the shell through holes passing therethrough and being electrically insulated from electrostatic shield.

10. The sensor of claim 5 wherein the shell does not have holes therethrough.

11. The sensor of claim 5 wherein the means for conducting the electrical current from the outside to the inside of the shell comprises an electrically-conductive area on each face to which conductors are attached, the conductive area on one end being in electrical contact with one set of electrodes and the conductive area on the other end being in electrical contact with the other set of electrodes.

12. A process for continuously measuring properties of a fluid material flowing in a process stream
   a. contacting a sensor wherein said sensor has a non-conductive shell having a bore therethrough, a pair of interdigitated fringing field electrodes on the inner surface of the shell, the electrodes being spaced from each other by 0.1 to 10 millimeters, an electrostatic shield on the outer surface, and means for conducting electrical current to one electrode and from the other electrode, with the fluid material, the sensor being positioned completely non-obstructively in the process stream;
   b. generating an electrical voltage difference to be applied to the electrodes;
   c. measuring the electrical current through the sensor;
   d. calculating capacitance, dissipation and dissipation factor; and
   e. comparing the calculated values to predetermined reference values.

13. The process of claim 12 wherein the fluid material is a molten polymer.

14. The process of claim 13 wherein the stream flowing through the sensor is the discharge from an extruder.

15. The process of claim 13 wherein the property being measured is melt viscosity or molecular weight.

16. Process of claim 13 wherein the polymer contains polar groups and the measured property is comonomer content of the polymer.

17. Process of claim 14 further comprising a means for continuously controlling at least one input to the extrusion process based on the calculated capacitance, dissipation and dissipation factor and the comparison of the calculated values to predetermined reference values. the comparison of the calculated values to predetermined reference values.

18. A sensor for making complex permittivity measurements in-line in a fluid conduit over a frequency range of about 0.5 to about 10,000 Hertz, said sensor comprising a non-conductive shell having a bore therethrough, a pair of interdigitated fringing field electrodes on the inner surface of the shell, an electrostatic shield on the outer surface, and means for conducting electrical current from one electrode and to the other electrode.

19. The sensor of claim 18 wherein the shell is cylindrical and the interdigitated fringing field electrodes are recessed into the inner surface of the shell sufficiently to be substantially flush with the inner wall of the shell.

20. The sensor of claim 19 wherein all materails used in the sensor are suitable for continuous service at temperatures greater than about 200° C.

21. The sensor of claim 18 wherein the sensor is placed in said fluid conduit without obstructing the flow of the process fluid.

22. The sensor of claim 18 wherein the sensor's electrodes are spaced from each other by 0.1 to 10 millimeters.

23. A process for continuously measuring properties of a fluid material flowing in a process stream comprising contacting the sensor of claim 18 with the fluid material operating the sensor over a fraquency range of about 0.5 to about 10,000 Hertz, generating an electrical voltage difference to be applied to the electrodes; measuring the electrical current through the sensor; calculating capacitance, dissipation and dissipation factor; and comparing the calculated values to predetermined reference values.

24. The process of claim 23 wherein the fluid material is a molten polymer.

25. The process of claim 23 wherein the property being measured is melt viscosity or molecular weight.

* * * * *